(12) United States Patent  
Imai et al.

(10) Patent No.: US 7,968,814 B2  
(45) Date of Patent: Jun. 28, 2011

(54) OPTICAL GRAIN SORTER

(75) Inventors: Takeshi Imai, Tokyo (JP); Norihiko Tanaka, Tokyo (JP)

(73) Assignee: Satake Corporation, Tokyo (JP)

( * ) Notice: Subject to any disclaimer, the term of this patent is extended or adjusted under 35 U.S.C. 154(b) by 335 days.

(21) Appl. No.: 12/230,102

(22) Filed: Aug. 22, 2008

(65) Prior Publication Data

US 2009/0050540 A1   Feb. 26, 2009

(30) Foreign Application Priority Data

Aug. 23, 2007   (JP) .................................. 2007-217552

(51) Int. Cl.
  *B07C 5/00*   (2006.01)
(52) U.S. Cl. ........ 209/580; 209/576; 209/644; 209/932; 382/110
(58) Field of Classification Search ................... 209/576, 209/580, 644, 932, 939; 382/110, 165
See application file for complete search history.

(56) References Cited

U.S. PATENT DOCUMENTS

| | | | |
|---|---|---|---|
| 5,318,173 A * | 6/1994 | Datari | 209/580 |
| 5,659,624 A * | 8/1997 | Fazzari et al. | 382/110 |
| 5,960,098 A * | 9/1999 | Tao | 382/110 |
| 6,100,488 A | 8/2000 | Satake et al. | |
| 6,391,354 B1 | 5/2002 | Shibayama et al. | |
| 7,130,461 B2 * | 10/2006 | Rosenholtz | 382/165 |
| 7,298,870 B2 | 11/2007 | Ikeda et al. | |
| 7,660,440 B2 * | 2/2010 | Bourg et al. | 382/110 |
| 2002/0008056 A1 | 1/2002 | Satake et al. | |
| 2005/0067332 A1 | 3/2005 | Ikeda et al. | |

FOREIGN PATENT DOCUMENTS

JP    2005-74412    3/2005

OTHER PUBLICATIONS

Search Report for corresponding British application GB0815479.1; search date, Nov. 28, 2008.

* cited by examiner

*Primary Examiner* — Joseph C Rodriguez
(74) *Attorney, Agent, or Firm* — Staas & Halsey LLP (57) ABSTRACT

A grain images obtained by CCD line sensors are processed by binarization processing to obtain contour images of grains and images of colored portions in the grains. The images are displayed on a monitor screen of an operating panel 30. The contour images and the images of the colored portions are displayed in a superposed state. Box frames generated by a highlight display circuit in control means 12 are simultaneously displayed by being superposed on the contour images having defective portions, thus producing a highlight display of defective grains. The defective grains include a grain having a light colored portion and a grain having a dark colored portion.

14 Claims, 10 Drawing Sheets

G0 NORMAL GRAIN
G1 GRAIN HAVING FIRST DEFECTIVE PORTION (DEFECTIVE GRAIN)
G2 GRAIN HAVING SECOND DEFECTIVE PORTION (DEFECTIVE GRAIN)
G3 FOREIGN OBJECT SUCH AS STONE

FIG. 10

- F0   CONTOUR IMAGE
- F1, F2   FIRST DEFECTIVE PORTION IMAGE
- F3   SECOND DEFECTIVE PORTION IMAGE
- D1   FIRST HIGHLIGHT DISPLAY
- D2   SECOND HIGHLIGHT DISPLAY
- D3   OPERATIVE NOZZLE INDICATING BAR
- D4   NOZZLE MOUTH CORRESPONDENCE LINE

OPTICAL GRAIN SORTER

BACKGROUND OF INVENTION

1. Field of the Invention

The present invention relates to an optical grain sorter used to sort out grains (defective grains) not normal in external appearance as a grain product from grain distributed on the market. More particularly, the present invention relates to an optical grain sorter of this kind arranged so that an operator can adjust a level of determination sensitivity (a threshold value set in the optical grain sorter) provided in the sorter for sorting normal grains (grains having a normal external appearance) and defective grains from each other, by seeing a display on a display device provided on the sorter.

2. Description of Related Art

In distribution of grain on the market, the commodity value should be improved by removing defective grains not normal in external appearance as grains. To do so, an optical grain sorter is used. However, while a certain degree of sorting suffices for avoiding any problem in terms of commodity value, there is a possibility of inappropriate setting of the level of sorting in some case of use of an optical grain sorter, depending on the kind or grade of grain or on the degree of cleaning. In such a case, it is necessary for an operator of the sorter to adjust the degree of sorting with the sorter as desired while checking the state of sorting with the sorter.

Figure 1:
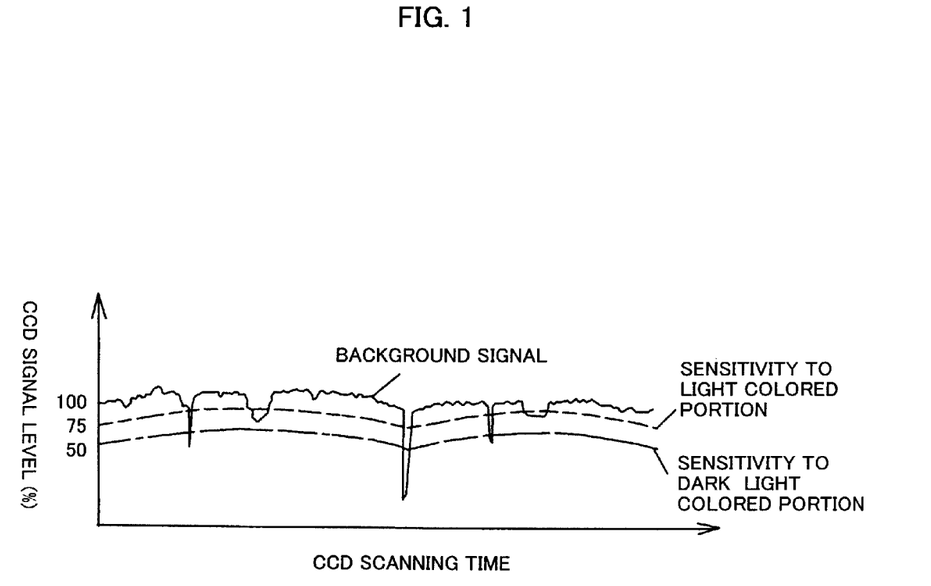
FIG. 1 is a diagram for describing the principle of grain sorting.

FIG. 1 shows the principle of grain sorting adopted in a conventional optical grain sorter. The grain sorting shown in FIG. 1 is sorting of cleaned rice grains. According to the principle, a grain from which a signal level corresponding to 75% or less of the background signal level assumed to be 100% is detected with a CCD line sensor is recognized as a grain having a light colored portion; a grain from which a signal level corresponding to 50% or less of the background signal level is detected is recognized as a grain having a dark colored portion; and these grains are determined as defective grains.

In the grain having a light colored portion, the light colored portion occupies at least a certain area in the grain surface such that this grain is discriminable from normal grains, and the degree of coloring of the colored portion is low (the color is light). In the grain having a dark colored portion, the deep colored portion has such a color in the grain surface that this grain is discriminable from normal grains, and the degree of coloring of the colored portion is high (the color is dark). The grain having a dark colored portion comprises any grain having a dark colored portion regardless of the area of the dark colored portion. The grain having a light colored portion and the grain having a dark colored portion are defective grains collectively called "colored grain".

In the conventional optical grain sorter, sorting of defective grains from normal grains is determination as to which drop in signal level from the signal level corresponding to normal grains with respect to the 100% background signal level indicates a defective grain. This is adjustment of a threshold value set in the optical grain sorter. Conventionally, the threshold value to be set is adjusted by seeing the actual state of sorting, displaying a signal from an optical sensor on an oscilloscope or touch panel monitor screen and seeing the signal.

An optical grain sorter described in Japanese Patent Laid-Open No. 2005-74412 displays on a monitor in an operating panel images of grains taken by image pickup means such as a CCD line sensor (binary data on the contours of grains), images of colored portions of grains having light colored portions (binary data on the shapes of the portions) and images of colored portions of grains having dark colored portions (binary data on the shapes of the portions). An operator of the sorter can determine whether or not defective grains are discriminated as expected by seeing the display on the monitor screen while seeing the actual state of sorting of grains.

The means adopted in the optical grain sorter described in Japanese Patent Laid-Open No. 2005-74412 has improved the trail-and-error condition in the conventional art using an oscilloscope when determination as to whether or not defective grains are discriminated as expected is required. That is, an operator of the optical grain sorter described in Japanese Patent Laid-Open No. 2005-74412 can directly grasp, as actual images of grains from a display on the monitor screen, the contours of grains and the sizes and shapes of colored portions in defective ones of the grains actually grasped by the optical grain sorter, instead of grasping them from a simple display of data on an oscilloscope. In this way, the facility with which a threshold value to be set in the optical grain sorter is set so that defective grains can be discriminated as expected is improved.

As a result, the operator can adjust the threshold value more efficiently in this sorter than in those previously proposed. Also, the accuracy of the threshold value is improved.

The means adopted in the optical grain sorter described in Japanese Patent Laid-Open No. 2005-74412 is excellent in that it enables an operator to adjust the threshold value for discrimination between normal grains and defective grains while seeing actual images of the grains on a monitor. However, it has a problem in terms of image display technique and, hence, the drawback of not facilitating discrimination between normal grains and defective grains displayed on the monitor. That is, the contours of a multiplicity of grains are displayed on one monitor screen, and colored portions of defective ones of the grains are displayed by being superposed on the contours of the grains, accompanied by their shapes and sizes. The images on the monitor are thus complicated, so that it is difficult to discriminate defective grains having light colored portions and defective grains having dark colored portions and there is a possibility of an operator failing to notice defective grains. It is necessary to unfailingly sort out defective grains having dark colored portions in particular. After the occurrence of failure to notice a defective grain having a dark colored portion and after the completion of sorting, the defective grain may be found in normal grains. Such an incident leads to a considerable reduction in reliability of the sorting process.

The technique for the optical grain sorter described in Japanese Patent Laid-Open No. 2005-74412 also has a problem that an operator is uncertain as to whether or not defective grains are correctly separated by air jet nozzles for separating defective grains from normal grains.

SUMMARY OF THE INVENTION

An object of the present invention is to provide an optical grain sorter capable of enabling an operator to clearly identify defective grains on a monitor screen of a display device.

Another object of the present invention is to provide an optical grain sorter capable of enabling an operator to clearly identify each of defective grains having light colored portions occupying a certain area or larger colored portions and defective grains having darker colored portions.

Still another object of the present invention is to provide an optical grain sorter capable of enabling an operator to check whether or not air jet nozzles corresponding to the positions of defective grains in a multiplicity of air jet nozzles prepared are correctively selected.

An optical grain sorter according to the present invention includes a fall-down path for passage of grains, image pickup means of electrically obtaining images of grains passing through the fall-down path, control means of processing image signals from the image pickup means, display means of displaying in a visually recognizable state the results of processing performed by the control means, and defective grain removal means and threshold value adjustment means operated on the basis of the results of processing performed by the control means.

The grain fall-down path is a path through which grains fall in the air, which is formed at an end of a slanting plate shooter or the like capable of transporting grains from an upper position to a lower position by spreading the grains so that the grains do not overlap each other, and which is formed of a multiplicity of parallel paths.

The image pickup means includes a CCD line sensor, a light source and a background plate. The image pickup means takes images of the background plate and grains irradiated with light from the light source.

The control means includes contour processing means of generating contours or the like of grains. The contour processing means processes image signals from the CCD line sensor to recognize the positions of grains on the fall-down path and to form images of the contours and colored portions of the grains. The images of the colored portions are formed by using two threshold values set in the control means and by discriminating light colored portions and dark colored portions. The two threshold values are determined on the basis of comparison between the amount of reflected light (background) from the background plate and the amount of reflected light from the grains. The positions of the colored grains are also recognized along with the positions of the grains.

The control means displays images of the contours and the colored portions of the grains on the display device. On the other hand, the control means selects some of a multiplicity of air jet nozzles to be operated on the basis of information on the positions of the colored grains. The selected air jet nozzles blow air jet toward the grains after a time lag corresponding to the time taken by the target grains to reach the nozzle position, thereby separating the color grains from the normal grains.

According to the present invention, the contours of the grains, the light colored portions and dark colored portions recognized by the control means are displayed in a superposed state on the monitor screen of the display device. Further, the control means includes defective portion highlight display means to display a mark for highlighting the existence of defective grains so that an operator can recognize the defective grains on the monitor screen at a glance.

The mark for highlighting the existence comprises a display using different colors and a display using a simple mark easily recognizable by the operator, e.g., a round, triangular or rectangular surrounding frame.

The threshold value adjustment means comprises an input device such as threshold value changing buttons disposed, for example, in the vicinity of the monitor screen of the display device, and a control circuit capable of increasing/reducing the threshold values set in the control means according to an input given via the input device.

Preferably, operative nozzle indication means are provided in the control means to also produce on the monitor screen of the display device a display indicating the position of the air jet nozzles selected by the control means to operate. This display enables the operator to determine whether or not the air jet nozzles corresponding to the fall-down paths through which the defective grains fall are correctly selected by the control means to separate the defective grains from the normal grains.

The optical grain sorter of the present invention enables the operator to easily and reliably check on the monitor screen the degree of defectiveness of the defective grains to be separated from the normal grains, i.e., on what criteria does the sorter operated by the operator evaluate the light colored portions and the dark colored portions in sorting out the defective grains. Therefore, the operator can easily perform a simulation for setting the threshold values in the defective grain removal means and the threshold value in the contour processing means and can accurately and efficiently determine the threshold values set in the optical grain sorter.

If means for storing image data displayed several past batches of image data displayed on the display device together with the threshold values set in correspondence with the past batches of image data and evoking the data when required is provided, the efficiency of the above-described simulation can be improved. In such a case, displays can be produced in a convenient manner, for example, in such a manner that the present data and past batches of data are simultaneously displayed in divided sections on the screen.

The present invention can be applied to sorting of other various kinds of grain such as wheat and soy beans by adjusting the necessary terms including the threshold values in the contour processing means and the defective grain removal means.

The contour processing means forms the contours of objects such as small stones mixed with grains as well as those of grains, so that foreign objects contained in grain at the time of harvest are also displayed on the monitor screen of the display device. It is, therefore, preferable to provide means for recognizing, for example, small stones from the contours of the same, displaying them in a highlighted state on the monitor screen and sorting out them from normal grains by the air jet nozzles in the same manner as in the case of sorting out defective grains.

While foreign objects such as pieces of glass and stones are identified as grains having dark colored portions, there is a possibility of failure to identify a piece of white plastic or the like as a foreign object in determination using visible light. To prevent this, near-infrared rays is used in addition to visible light. Grains and plastics reflect near-infrared rays in largely different ways. Therefore, grains and plastics can be discriminated from each other by using near-infrared rays. There is a need for means for processing images formed by near-infrared rays.

In some case, the accuracy of sorting out defective grains is also influenced by the rate of flow of the raw-material (grains before sorting). It is, therefore, convenient to display the current rate of flow of the raw material on the display device. To measure the current rate of flow the raw material, means for computing the raw material flow rate from the entire area of the monitor screen of the display device and the proportion of the area occupied by the contour images of grains in the entire area of the monitor screen may be used. Simpler means of counting the number of grains passing through the fall-down path may alternatively be used.

The image displayed on the display device may be either a still image or moving image. In the case of displaying a moving image, contour images of a large number of grains are moved in one direction on the screen and a display of colored portions and a display of marks for highlighting the existence of the colored portions are superposed thereon while being moved.

DETAILED DESCRIPTION

Figure 2:
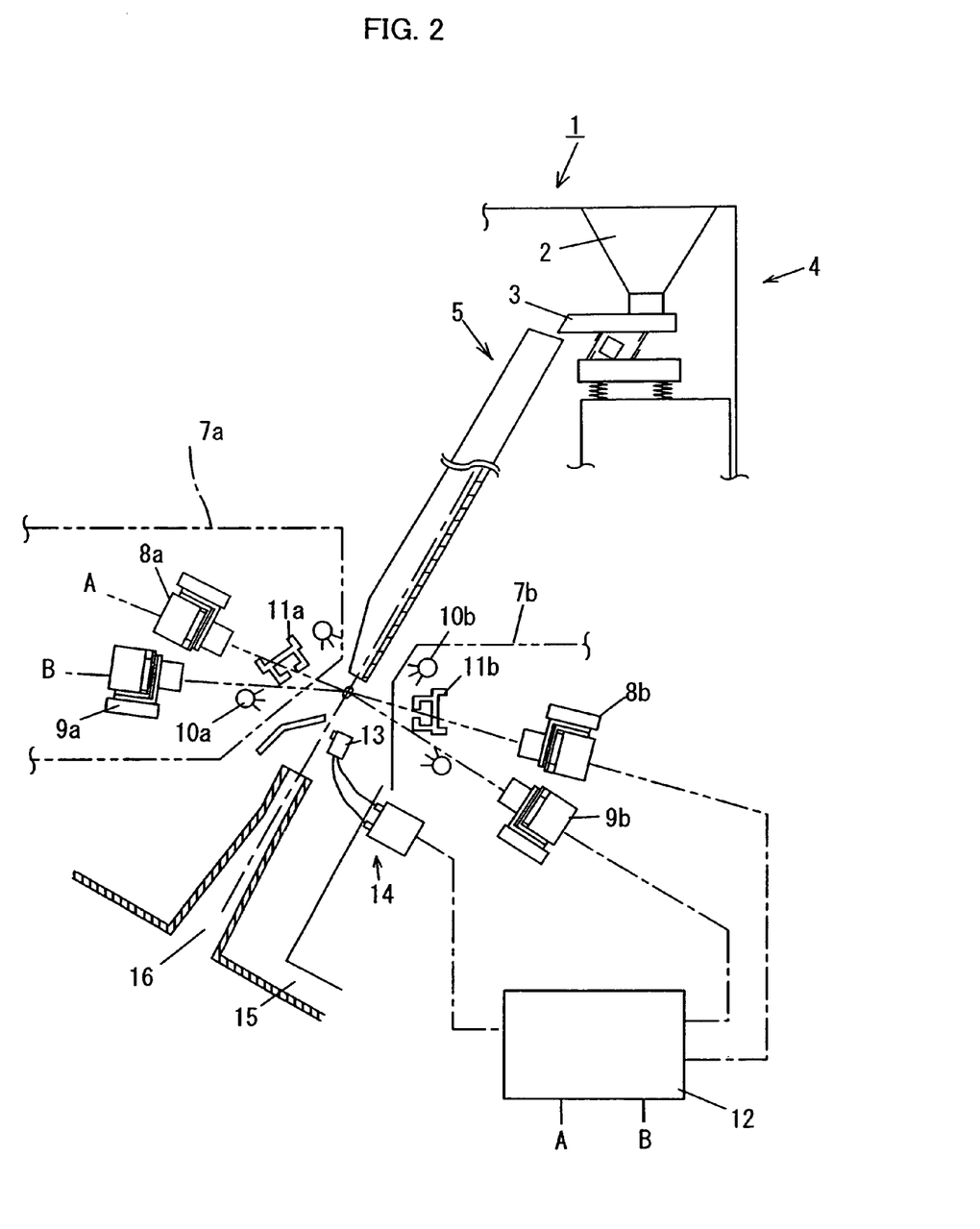
FIG. 2 is a side view for outlining an optical grain sorter.
Figure 3A:
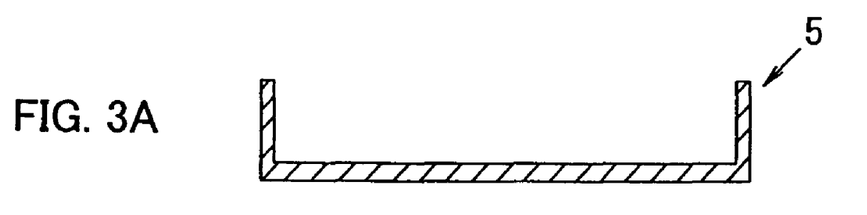
FIGS. 3A and 3B are transverse sectional views of a slanting shoot.
Figure 3B:
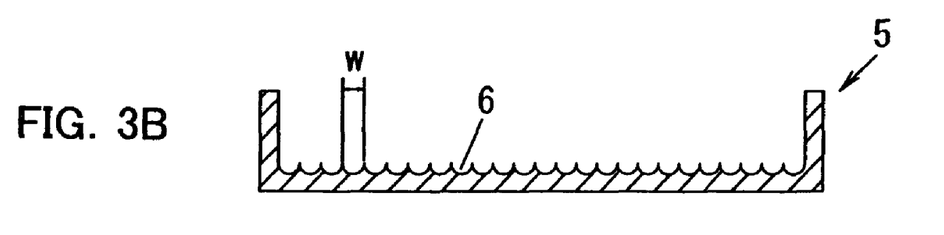

FIG. 2 schematically shows essential internal structural portions of an optical grain sorter 1 which is an embodiment of the present invention. The optical grain sorter 1 has, at an upper position therein, a grain supply portion 4 including a tank 2 and a vibrating feeder 3. Grains supplied from the grain supply portion 4 (polished grains in the present embodiment) flow continuously downward onto a slanting shoot 5 by gravity. On the slanting shoot 5 having a predetermined shape, grains can flow downward while spreading laterally widely. The grains are let fall from the lower end of the slanting shoot into the air by taking a multiplicity of columnar fall-down paths parallel to each other. In the present embodiment, the slanting shoot 5 has flat shooting surface, as shown in FIG. 3A. However, the shooting surface may have a multiplicity of flow-down grooves 6 each having a width close to the width W of grains, as shown in FIG. 3B. It is preferable to provide such grooves because they are effective in making the falling attitudes of grains uniform.

At least a pair of image pickup means 7a and 7b are provided generally symmetrically about the multiplicity of parallel fall-down paths. These means are illustrated in areas indicated by the double-dot-dash lines in FIG. 2. The image pickup means 7a includes CCD line sensors 8a and 9a in cameras, a lamp 10a and a background plate 11a. The other image pickup means 7b includes CCD line sensors 8b and 9b in cameras, a lamp 10b and a background plate 11b. The CCD line sensors 8a, 9a, 8b, and, 9b of the image pickup means 7a and 7b take images of grains reaching a detection position O in the fall-down paths and send signals for the images to control means 12 described below in detail.

In the present embodiment, the image pickup means 7a and 7b are disposed on opposite sides of the grain fall-down paths to obtain original images of grains through reflected light from front and back surfaces of the grains. However, image pickup means may alternatively be disposed on only one side of the grain fall-down paths.

The control means 12 determines the contour (outline) of each grain and identifies a defective grain on the basis of the image signals from the CCD line sensors. When the control means 12 recognizes a defective grain, it generates a removal signal and sends the removal signal for an opening/closing valve in a removal device 14 including air jet nozzles 13. The removal device 41 receives the removal signal and opens the opening/closing valve to blow an air jet toward the grain fall-down path, thereby separating from the fall-down path the defective grain determined to be removed by generating the removal signal. Defective grains sorted out in this way are expelled from the sorter through a defective grain discharge port 15. Normal grains that have passed through the fall-down paths without being acted on by the removal device 14 are recovered through a nondefective discharge port 16.

Figure 4:
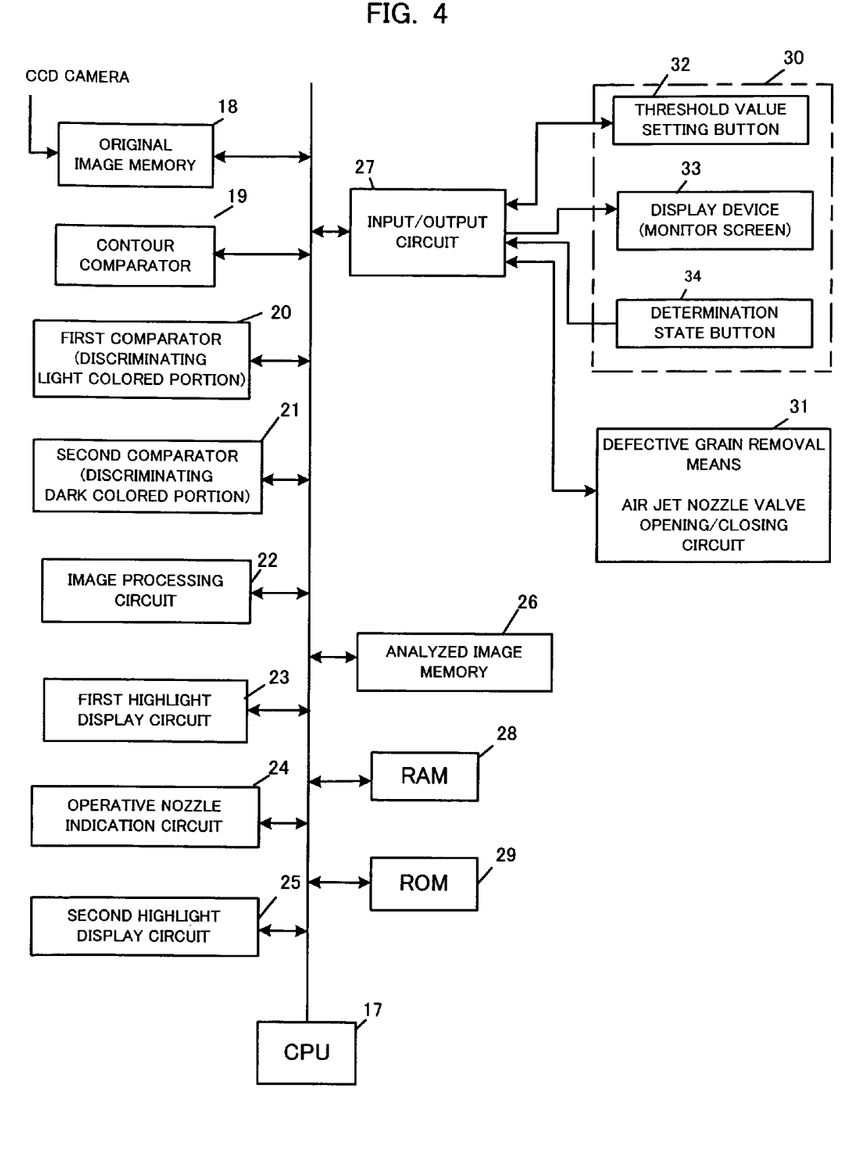
FIG. 4 is a block diagram showing essential points of control means.

The control means 12 is constituted mainly by a central processing unit (CPU) 17. On the bus of the CPU 17 are provided an original image memory 18, a contour comparator 19, a first comparator 20, a second comparator 21, an image processing circuit 22, a first highlight display circuit 23, an operative nozzle indication circuit 24, a second highlight display circuit 25, an analyzed image memory 26, an input/output circuit 27, a random-access memory (RAM) 28 and a read-only memory (ROM) 29. An operating panel 30 and sorting means 31 are connected as external devices to the input/output circuit 27. The operating panel 30 includes a display device 33 having threshold value setting buttons 32 and a monitor screen. The defective grain removal means 31 includes the air jet nozzles 13 of the removal device 14 and a valve opening/closing circuit for driving the air jet nozzles 13.

Figure 5:
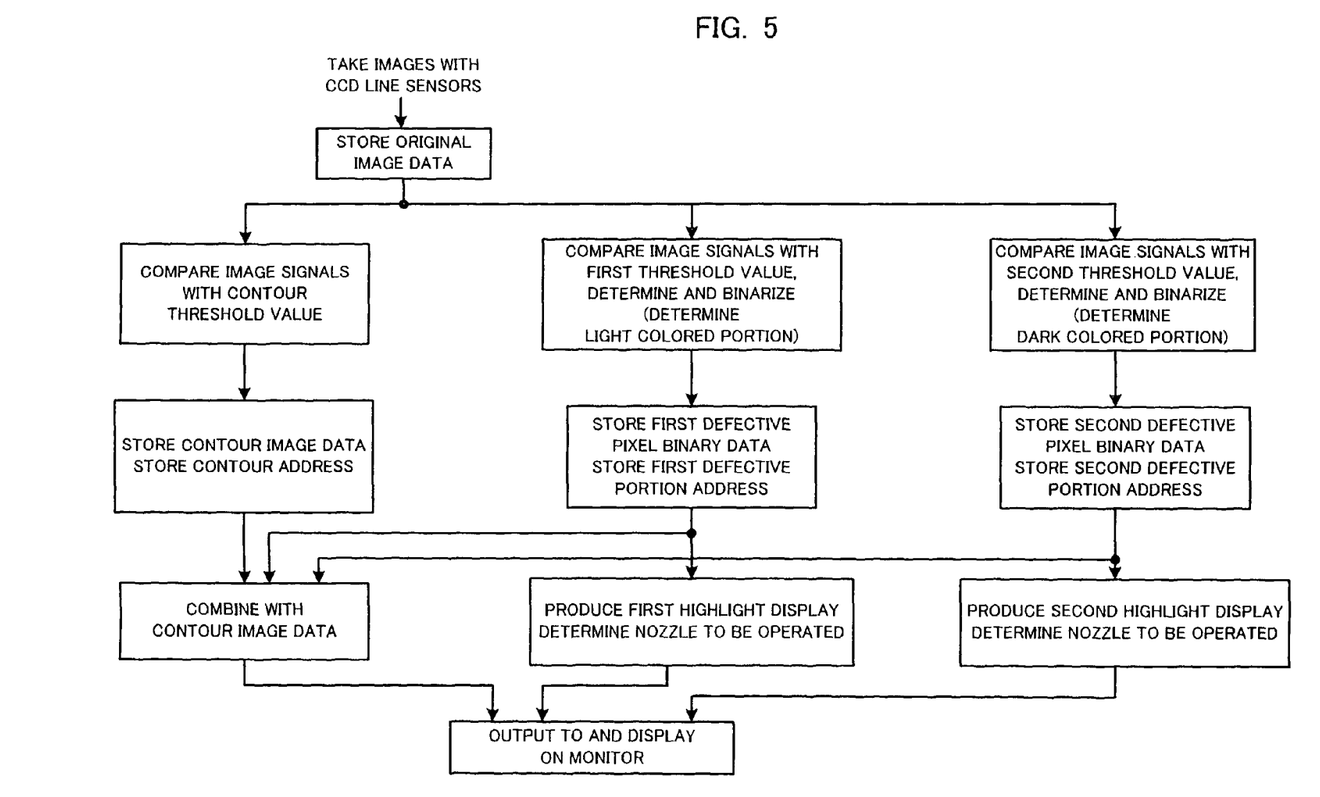
FIG. 5 is a diagram showing the outline of processing in the control means.

The CPU 17 organically connects and controls these components (circuits) according to a predetermined program stored in the ROM 29. FIG. 5 shows the outline of the connection and control. Description will be made of the connection and control with reference to FIGS. 4 and 5.

The RAM 28 is a temporary storage required in data processing performed by the CPU 17.

The original image memory 18 is a RAM having a memory capacity necessary for forming the monitor screen of the display device 33. The original image memory 18 takes in the image signals from the CCD line sensors 8a, 8b, 9a, and 9b in correspondence with predetermined clock cycles set in the control means 12. Image data in the original image memory 18 is updated by the first-in first-out method at all times.

The contour comparator 19 analyzes contour images of grains by comparing image data read out from the original image memory 18 with a contour threshold value for discrimination of the contours of the grains, and outputs binary data representing the external shapes of the grains. Contour images are formed in the image processing circuit 22 on the basis of this data. The contour images are stored in a contour area in the analyzed image memory 26 together with addresses indicating the positions of the grains on the monitor screen.

The first comparator 20 analyzes colored portions of grains by comparing the image data read out from the original image memory 18 with a first threshold value for recognition of a light colored portion, and outputs the results of the analysis as first defective pixel binary data. First defective portion images are formed in the image processing circuit 22 on the basis of this data. The first defective portion images are stored in a light colored portion area in the analyzed image memory 26 together with addresses indicating the positions on the monitor screen in the display device 33. The first comparator 20 is the first defective portion determination means.

The second comparator 21 analyzes colored portions of grains by comparing the image data read out from the original image memory 18 with a second threshold value for recognition of a dark colored portion, and outputs the results of the analysis as second defective pixel binary data. Second defective portion images are formed in the image processing circuit 22 on the basis of this data. The second defective portion images are stored in a colored grain area in the analyzed image memory 26 together with addresses indicating the positions on the monitor screen. The second comparator 21 is the second defective portion determination means.

The light colored portion discriminated by the first comparator 20 is, for example, in the present embodiment, a portion having a brightness level of 75 or less with respect to the brightness of the background plates 11a and 11b assumed to be 100, while the dark colored portion is a portion having a brightness level of 50 or less. However, a determination as to whether or not the light colored portion occupies an area equal to or larger than a set area in the contour image of the grain is also made in the image processing circuit 22. Only the existence is determined with respect to the dark colored portion.

The first highlight display circuit 23 generates a box frame (rectangular mark) in the present embodiment to explicitly show an operator the position of a first defective portion image on the monitor screen of the display device 33. The box frame is displayed by being superposed on the first defective portion. Any other highlight display method, e.g., a method of showing a first defective portion in a conspicuous color such as a brilliant color, a method of indicating by an arrow, or a method of displaying a defective portion in a blinking manner may alternatively be used.

This circuit generates frame data when receiving an instruction from the CPU 17, and displays the frame data on the monitor screen of the display device 33 on the basis of the address obtained from the first comparator 20. In the present embodiment, the box fame has such a frame shape tangent to the grain contour.

Similarly, the second highlight display circuit 25 produces a highlight display on a second defective portion. The first highlight display and the second highlight display may differ from each other. For example, a rectangular frame is superposed on a first defective portion, while a triangular frame is superposed on a second defective portion. Also, frame in different colors may be used. The first highlight display circuit 23 and the second highlight display circuit 25 constitute the defective portion highlighting means.

The operative nozzle indication circuit 24 is means for explicitly informing the operator that each of the air jet nozzles 13 for removing defective grains is correctly recognized in the optical grain sorter 1. A method for indication of this use, for example, a noticeable bar in red displayed by being superposed on the contour of a defective grain. When an instruction is sent from the CPU 17 to the operative nozzle indication circuit 24, the operative nozzle indication circuit 24 prepares bar data about the position of the air jet nozzle selected by the control means to be operated and displays the bar data on the monitor screen of the display device 33 on the basis of the address obtained from the first comparator 20 and the second comparator 21. That is, a red bar indicating that the air jet nozzle corresponding to a defective grain is selected is displayed by being superposed on the image of the defective grain. The operative nozzle indication circuit 24 is the operative nozzle indication means.

When a determination state button 34 (FIG. 10) in the operating panel 30 is pressed, an image output command to output an image to the monitor screen of the display device 33 is input through the input/output circuit 27 to be transmitted to the CPU 17. The CPU 17 then produces a combined image on the basis of a program stored in the ROM 29 by sending image data from the analyzed image memory 26, data from the first and second highlight display circuits 23 and 25 and data from the operative nozzle indication circuit 24 to the image processing circuit 22, and displays the image on the monitor screen of the display device 33 through the input/output circuit 27. On the monitor screen, contour images of grains are displayed and images of light-colored portions and dark colored portions are displayed by being superposed on the contour images. Also, box frames are displayed by being superposed on the defective grains having the light colored portions and the defective grains having the dark colored portions. Further, if execution of the operation of the air jet nozzles 13 corresponding to these defective grains has been determined, red bars extending laterally are displayed so as to extend across the contour images of the grains.

The threshold value setting buttons 32 in the operating panel 30 can be operated to change parameter values relating to the threshold values of the first and second comparators 20 and 21 set in the RAM 28 through the input/output circuit 27.

To the valve opening/closing circuit of the defective grain removal means 31, valve opening signals from the CPU 17 only for the air jet nozzles 13 corresponding to the defective grains are supplied by being delayed from the moment at which the grains pass through the position of the CCD line sensor by a time period determined by the distance to the positions of the air jet nozzles 13 and the falling speed. This supply timing and the selection of the air jet nozzles 13 are based on the program and set values stored in the ROM 29.

Figure 6:
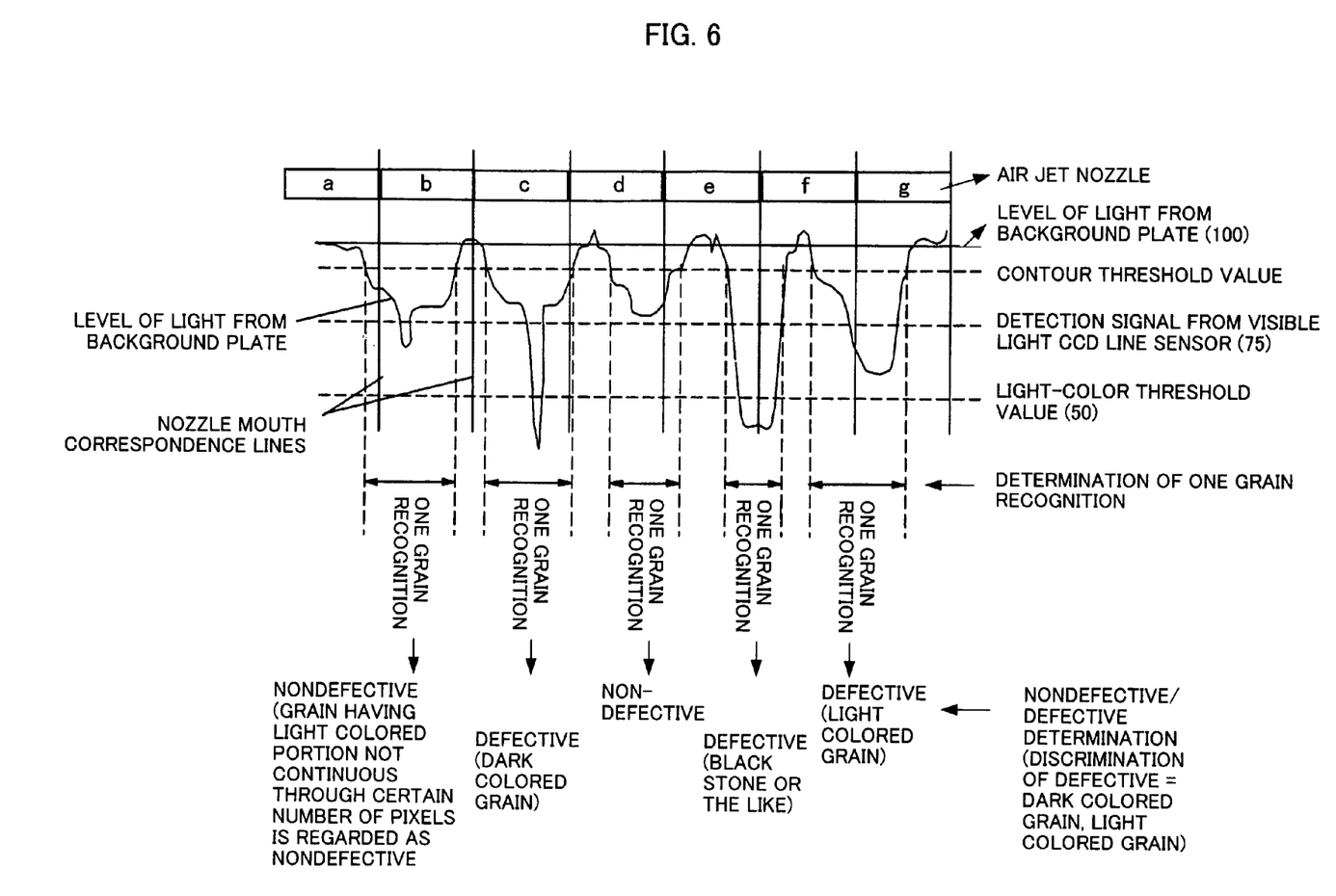
FIG. 6 is a diagram for describing a determination method.
Figure 7:
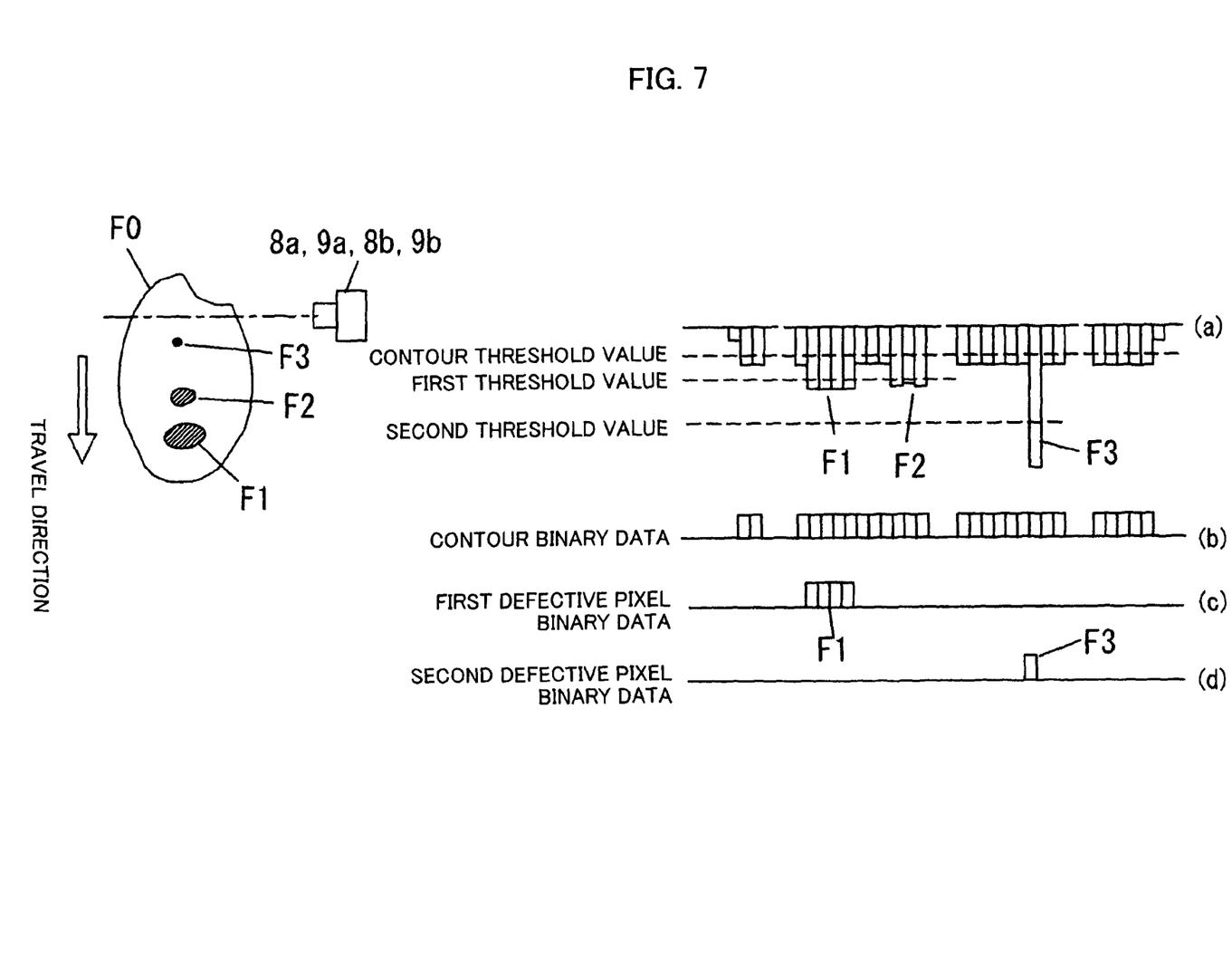
FIG. 7 is another diagram for describing the determination method.

FIGS. 6 and 7 are diagrams for explaining how the contours, light colored portions and dark colored portions of grains are detected. FIG. 7 schematically shows values and data with respect to FIG. 6. In (a) of FIG. 7, the signal level from, for example, the CCD line sensor 8a when grains pass the CCD line sensor 8a scanning line is shown. The signal level is changed into binary data by the contour comparator 19, the first comparator 20 and the second comparator 21 in the control means 12.

The contours of grains are first detected with reference to the contour threshold value set to the lowest level. Signals representing the detection results are sent as contour binary data representing the contours of grains as shown in (b) of FIG. 7 to the analyzed image memory 26 in the subsequent stage.

With respect to a grain having two light colored portions F1 and F2 differing in area from each other, signals exceeding the first threshold value corresponding to the light colored portions appear in two places in the signal level graph shown in (a) of FIG. 7 in correspondence with the portions F1 and F2. The area of each colored portion corresponds to the number of pixels. It can be understood that the number of pixels of the light colored portion F1 appearing first in the travel direction is 4 and the number of pixels of the light colored portion F2 appearing next is 3. In the present embodiment, the signal output from the first comparator 20 is set so as to express a defective grain only when the number of pixels of a light colored portion is four or more. As a result of this setting, only an amount of data corresponding to the colored portion F1 appears as first defective pixel binary data representing a defective portion exceeding the first threshold value, as shown in (c) of FIG. 7. This data is sent to the analyzed image memory 26 in the subsequent stage. A grain having a light colored portion of a comparatively small area, e.g., one having only the portion F2 is treated as a normal grain. Such a grain has no problem as a commodity. Thus, the above-described processing increases the yield of the sorting operation.

With respect to a grain having a dark colored portion F3, a signal exceeding the second threshold value corresponding to the dark colored portion appears in the signal level graph shown in (a) of FIG. 7 in correspondence with the portion F3. In this case, since a dark colored portion exists, the grain is determined to be defective regardless of the area of the colored portion. A signal representing this detection result is sent to the analyzed image memory 26 as second defective pixel binary data representing a defective portion exceeding the second threshold value, as shown in (d) of FIG. 7.

The description has been made with respect one grain having two light colored portions differing in area from each other and another grain having one dark colored portion. In actuality, however, the number of colored portions varies largely among grains.

Figure 8:
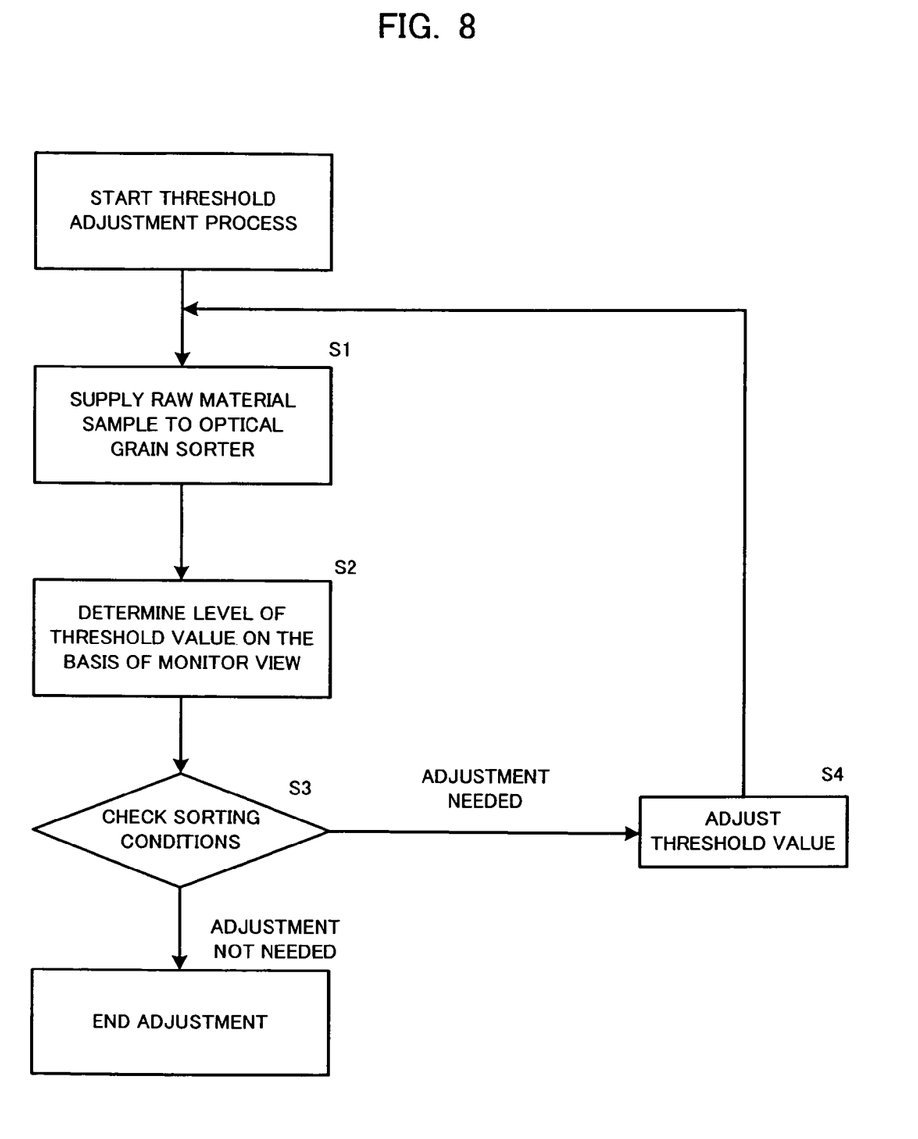
FIG. 8 is a diagram showing a procedure for user operations.
Figure 9:
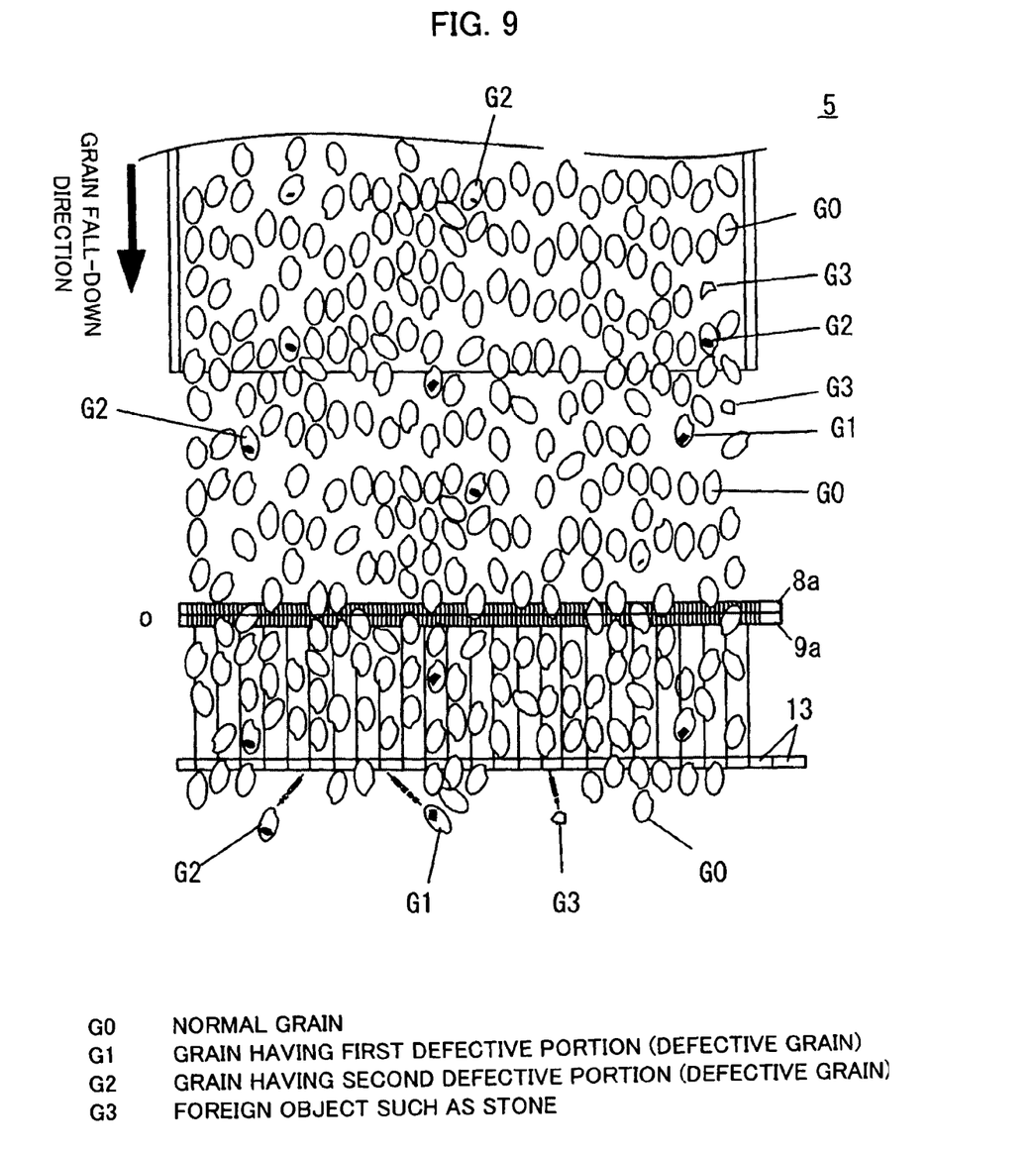
FIG. 9 is a front view showing a flow-down state of grains.
Figure 10:
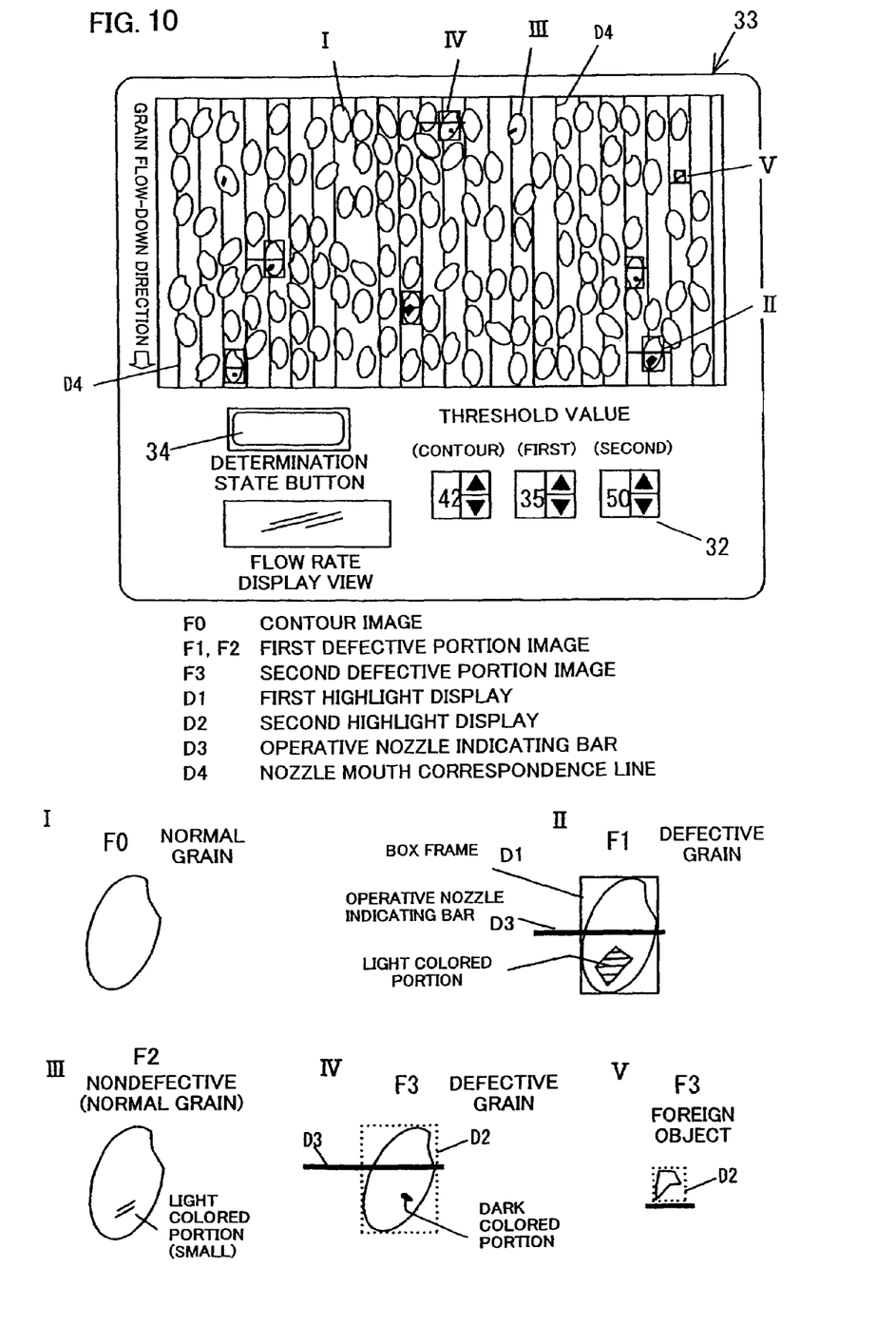
FIG. 10 is a diagram showing an example of a view on a monitor screen of a display device.

FIG. 8 shows the flow of a grain sorting condition adjustment process performed by an operator before operating the optical grain sorter 1. The optical grain sorter 1 is started to supply a raw material (grains before sorting) to the tank 2 (step S1). Images of grains falling along the slanting shoot 5 (FIG. 9) are taken at the detection position O in the fall-down paths by the CCD line sensors 8a, 9a, 8b, and 9b. The taken images are processed by the control means 12 as described above to be displayed on the monitor screen of the display device 33 in the operating panel 30 (FIG. 10). In FIG. 9, G0 denotes a normal grain; G1, a grain having a light colored portion (defective grain); G2, a grain having a dark colored portion (defective grain); and G3, a foreign object such as a small stone. G3 can be identified as a foreign object because of its external shape different from that of grains.

On the monitor screen shown in FIG. 10 are displayed a contour image F0 of a grain, an image F1 or F2 of a light colored portion, an image F3 of a dark colored portion, a first highlight display (box frame and coloring) D1, a second highlight display D2 (box frame and coloring), and an operative nozzle indicating bar D3 (in red in actuality). D4 indicates nozzle mouth correspondence lines fixedly displayed on the monitor screen. The distance between the nozzle mouth correspondence lines D4 corresponds to the mouth width of the air jet nozzles 13. In the case where the flow-down grooves 6 are formed in the slanting shoot 5, the distance between the nozzle mouth correspondence lines D4 also corresponds to the width of the grooves 6. When a defective grain falls through such a position as to cross one nozzle mouth correspondence line D4, and when the air jet nozzles 13 on the opposite sides of the nozzle mouth correspondence line D4 are operated, an elongated operative nozzle indicating bar D3 is displayed on the monitor screen of the display device 33 so as to cross the nozzle mouth correspondence line D4 and extend between the nozzle mouth correspondence lines D4 on the opposite sides in order to indicate the falling state of the grain and the operation of the air jet nozzles 13. In a case where a defective grain crosses one nozzle mouth correspondence line D4 to only a small extent (e.g., an extent corresponding to 2 or 3 pixels on the monitor screen), an operative nozzle indicating bar D3 is displayed only between the adjacent pair of nozzle mouth correspondence lines D4 on the chief air jet nozzle 13 side. Preferably, the operator is enabled to make a setting or selection as to the extent of crossing related to the operation of the air jet nozzles on the opposite sides or as to whether or not the bar is displayed between the adjacent pair of nozzle mouth correspondence lines D4.

The frame for the first highlight display D1 and the frame for the second highlight display D2 may be made different in color or shape from each other to facilitate discrimination therebetween.

Thus, the operator can clearly grasp the state of determination of defective grains (including foreign objects) in the optical grain sorter. The operator compares the sorting conditions set in the sorter and known from the monitor screen of the display device 33 with the actual sorting results to determine whether or not the present threshold value set by the operator is suitable (step S3). If there is a need for adjustment, the operator operates the threshold value setting buttons 32 provided in the operating panel 30 to adjust the threshold values (step S4) and returns the process to step S1 to repeat the same operations and continue adjustment. This process is repeated until the need for adjustment is eliminated.

The proportion of grains sorted out as defective grains as a result of changing the threshold values can be simulated on the monitor screen of the image display device 33 at the time of threshold value adjustment (step S4). Therefore the results of adjustment can be easily compared with the actual state of sorting and the target threshold values can easily be reached.

After the completion of adjustment, the steady operation is performed.

Indication of the operative nozzle display bar D3 simultaneously superposed on a defective grain enables the operator to confirm that the air jet nozzle 13 for removing the defective grain is recognized in the optical grain sorter 1. The position of the air jet nozzle 13 actually operated may be checked on the basis of this confirmation. A trouble on the air jet nozzle side can be easily found in this way.

In the present embodiment, threshold values for contour images (contours), light colored portions and dark colored portions can be individually adjusted separately from each other. The adjusted threshold values are respectively transmitted to the control means 12 via the input/output circuit 27 to change the parameters set in the RAM 28 in association with the threshold values.

A moving image corresponding to the above-described image may alternatively be displayed on the monitor screen of the display device 33. In such a case, the amount of data corresponding to one monitor view 33 (frame-by-frame basis) is taken from the original image memory 18 into a frame storage area of a RAM according to the first-in first-out method under the control of the CPU 17, and contour images and the above-described two kinds of colored portions are formed by means of the first and second comparators 19, 20 and 21 on the basis of the data taken in the RAM. These kinds of images are accumulated in the analyzed image memory 26 and thereafter displayed on the monitor screen. On the other hand, the addresses for defective portions are transmitted from the first and second comparators to the CPU 17, and box frames or the like generated in the first and second highlight display circuits 23 and 25 and bars indicating selected ones of the air jet nozzles are displayed on the monitor screen. These frame displays are successively repeated in short cycles to form a moving image.

What is claimed is:

1. An optical grain sorter comprising:
   a transport device to continuously transport grains while widely spreading the grains;
   a defective grain removal device including air jet nozzles disposed in correspondence with grain fall-down paths formed at an end of the transport device;
   an image pickup device to take images of the grains at a detection position set in the fall-down paths;
   a contour comparator to output the contours of the grains as contour binary data on the basis of a comparison between image signals from the image pickup device and a contour threshold value set in advance;
   a defective portion determination device to compare the image signals from the image pickup device with a threshold value corresponding to a density and outputting as defective pixel binary data, a defective portion exceeding the threshold value and having an area equal to or larger than a set area;
   a grain display device to combine the contour binary data from the contour comparator and the defective pixel binary data from the defective portion determination device, and displaying the combined data on a monitor screen of a display device;

a defective grain determination device to inform the defective grain removal device of any one of the grains having a colored portion in the contour as a grain to be removed;

a defective portion highlight display device to produce a highlight display of the defective pixel binary data from the defective portion determination device on the monitor screen of the display device;

a threshold value adjustment device; and an operative nozzle display device to indicate the position of any one of the air jet nozzles operated in correspondence with one of the grains having a colored portion.

2. The optical grain sorter according to claim 1, further comprising an image memory to store the contour binary data and the defective pixel binary data.

3. The optical grain sorter according to claim 1, wherein the defective portion determination device includes a first defective portion determination device to output as first defective pixel binary data, a first defective portion exceeding a first threshold value corresponding to a first density and having an area equal to or larger than the set area, and a second defective portion determination device to output as second defective pixel binary data, a second defective portion exceeding a second threshold value corresponding to a second density higher than the first density.

4. The optical grain sorter according to claim 3, wherein the first defective pixel binary data represents a light colored portion, and the second defective pixel binary data represents a dark colored portion.

5. The optical grain sorter according to claim 1, wherein the defective portion highlight display device displays the first defective portion and the second defective portion in different highlight displays.

6. The optical grain sorter according to claim 5, wherein a box frame is used as one highlight display mark.

7. The optical grain sorter according to claim 1, wherein the operative nozzle display device indicates the position of any one of the air jet nozzles selected by a controller to be operated, by displaying a bar having a length corresponding to the width of the air jet nozzle while superposing the bar on the display of the defective grain.

8. The optical grain sorter according to claim 1, further comprising a selector to make a selection, when one of the grains determined as a defective grain overlaps an adjacent pair of the air jet nozzles, as to whether one of the air flow nozzles having a larger amount of overlap on the grain or both the air flow nozzles are operated.

9. The optical grain sorter according to claim 2, wherein the defective portion determination device includes a first defective portion determination device to output as first defective pixel binary data, a first defective portion exceeding a first threshold value corresponding to a first density and having an area equal to or larger than the set area, and a second defective portion determination device to output as second defective pixel binary data, a second defective portion exceeding a second threshold value corresponding to a second density higher than the first density.

10. The optical grain sorter according to claim 2, wherein the defective portion highlight display device displays the first defective portion and the second defective portion in different highlight displays.

11. The optical grain sorter according to claim 3, wherein the defective portion highlight display device displays the first defective portion and the second defective portion in different highlight displays.

12. The optical grain sorter according to claim 4, wherein the defective portion highlight display device displays the first defective portion and the second defective portion in different highlight displays.

13. The optical grain sorter according to claim 2, further comprising a selector to make a selection, when one of the grains determined as a defective grain overlaps an adjacent pair of the air jet nozzles, as to whether one of the air flow nozzles having a larger amount of overlap on the grain or both the air flow nozzles are operated.

14. The optical grain sorter according to claim 3, further comprising a selector to make a selection, when one of the grains determined as a defective grain overlaps an adjacent pair of the air jet nozzles, as to whether one of the air flow nozzles having a larger amount of overlap on the grain or both the air flow nozzles are operated.

* * * * *